United States Patent [19]

Phillips

[11] Patent Number: 4,710,582

[45] Date of Patent: Dec. 1, 1987

[54] HERBICIDALLY ACTIVE SUBSTITUTED DIPHENYL ETHER OXIME DERIVATIVES

[75] Inventor: James G. Phillips, Medina, Ohio

[73] Assignee: PPG Industries, Inc., Pittsburgh, Pa.

[21] Appl. No.: 885,359

[22] Filed: Jul. 14, 1986

[51] Int. Cl.⁴ ............................................ C07C 101/00
[52] U.S. Cl. ........................................ 560/35; 71/108; 71/111; 71/116; 562/440
[58] Field of Search ................... 560/35; 71/108, 111, 71/116; 562/440

[56] References Cited

FOREIGN PATENT DOCUMENTS

| | | | |
|---|---|---|---|
| 0003416 | 10/1978 | European Pat. Off. | 560/21 |
| 0003295 | 1/1979 | European Pat. Off. | 560/21 |
| 3017795 | 11/1980 | Fed. Rep. of Germany | 560/35 |

*Primary Examiner*—Paul J. Killos
*Attorney, Agent, or Firm*—Edward J. Whitfield

[57] ABSTRACT

This invention relates to certain substituted diphenyl ether oxime derivatives and to the use of same to control the growth of noxious plants, i.e., weeds.

5 Claims, No Drawings

HERBICIDALLY ACTIVE SUBSTITUTED DIPHENYL ETHER OXIME DERIVATIVES

FIELD OF THE INVENTION

This invention relates to certain substituted diphenyl ether oxime derivatives and to the use of the same to control the growth of noxious plants, i.e., weeds.

DESCRIPTION OF THE INVENTION

This invention provides herbicidally active substituted diphenyl ether oxime compounds represented by the Formula I:

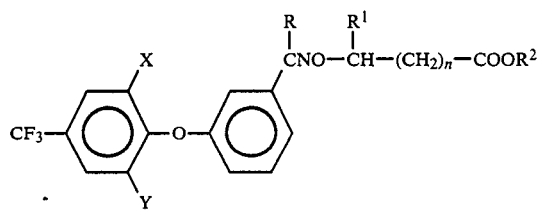

wherein:
X and Y are the same or different halogen;
R is hydrogen, halogen, cyano, $C_1$ to $C_4$ alkyl or haloalkyl, $C_1$ to $C_4$ alkoxy or alkylthio, or mono or dialkylamino;
$R^1$ is hydrogen or $C_1$ to $C_4$ alkyl;
$R^2$ is hydrogen or up to $C_{10}$ alkyl, haloalkyl, cycloalkyl, alkenyl, alkynyl, alkoxyalkyl or phenyl, substituted phenyl, benzyl or substituted benzyl; and
n is 0, 1, 2 or 3.

It is, of course, understood that agronomically acceptable salts of the Formula I compounds are within the scope of this invention, e.g., compounds wherein $R^2$ is an alkali metal ion, ammonium or substituted ammonium ion. Stereo and optical isomers of the Formula I compounds are also included.

Suitable alkyl radicals of which the various 'R' groups are representative include methyl, ethyl, n-propyl, iso-propyl, n-butyl, t-butyl or iso-butyl. Chloromethyl, chloroethyl, dichloroethyl, bromomethyl, bromoethyl, trifluoromethyl, trifluoroethyl, trichloromethyl and the like are exemplary haloalkyls. As examples of alkoxy and alkylthio radicals there may be mentioned methoxy, ethoxy, propoxy, methylthio, ethylthio or the like. Mono or dialkyl amino groups include methylamino, dimethylamino, methylethylamino, diethylamino or the like. Halogens represented by X and Y include bromine, chlorine or fluorine. Sodium, potassium or lithium, preferably sodium or potassium, are exemplary of alkali metal ions represented by $R^2$.

Preferred compounds of the Formula I are wherein X and Y are fluorine or chlorine; R is alkyl or haloalkyl; $R^1$ is hydrogen; $R^2$ is alkyl or haloalkyl; and n is 0.

Compounds of the Formula I may be prepared using techniques known to and starting materials available to the art. For example, a Formula I compound may be prepared by reacting an appropriately substituted diphenyl ether oxime of the Formula II:

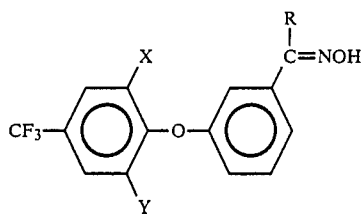

wherein X, Y, and R are as previously defined, with an appropriately substituted haloalkanoic acid or ester of the Formula III:

wherein $R^1$, $R^2$ and n are as previously defined and Hal is halogen, preferably, bromine or chlorine.

The following Examples are illustrative of the preparation of a certain compound of this invention.

EXAMPLE I

Preparation of:
3-(2-chloro-6-fluoro-4-trifluoromethylphenoxy) acetophenone oxime-0-(acetic acid, methyl ester)

7.5 Grams of 3-(2-chloro-6-fluoro-4-trifluoromethylphenoxy) acetophenone oxime was dissolved in 150 milliters of dry tetrahydrofuran and cooled to 0° C. under a nitrogen blanket. 1.2 Grams of sodium hydride were added and the reaction mixture was stirred for 15 minutes. To the stirred reaction mixture were added 3.3 grams of methyl bromoacetate and stirring was continued for one hour, the reaction mixture having warmed to room temperature. The reaction was then poured into 100 milliliters of water and extracted with 150 milliliters of diethylether. After, drying over anhydrous magnesium sulfate, the organic phase was stripped of solvent in vacuo, affording a yellow oil which crystallized on standing. The crystalline solid was twice recrystallized from hexane affording a total of 5.6 grams of recrystallized material confirmed by NMR and MS analyses as the desired product.

EXAMPLE II

Preparation of:
3-(2,6-dichloro-4-trifluoromethylphenoxy) acetophenone oxime-0-(acetic acid, methyl ester)

To 10 milliliters of dimethyl sulfoxide were added, under a nitrogen blanket, 1.39 grams of 3-(2,6-dichloro-4-trifluoromethylphenoxy) acetophenone oxime and 0.66 gram of potassium carbonate. To the stirred reaction mixture was added 0.57 gram of methyl bromoacetate and stirring was continued for 24 hours at room temperature. The reaction mixture was then poured into water and extracted with diethyl ether. The organic phase was then stripped of solvent in vacuo, affording a yellow oil. The oil was charged to a column containing 30 grams of silica gel and eluted with a 1:9 v/v mixture of ethyl acetate:hexane. Solvent removal afforded 0.65 gram of white solid, confirmed by NMR and MS analyses, as the desired product.

EXAMPLE III

Preparation of:
3-(2,6-difluoro-4-trifluoromethylphenoxy)
acetophenone oxime-0-(acetic acid, methyl ester)

1.5 Grams of 3-(2,6-difluoro-4-trifluoromethylphenoxy) acetophenone oxime was dissolved in 20 milliliters of dry tetrahydrofuran and cooled to 0° C. under a nitrogen blanket. 0.25 Gram of sodium hydride was added, followed in 5 minutes by the addition of 0.67 gram of methyl bromoacetate. The reaction mixture was stirred for one hour by which time it had warmed to room temperature. The reaction mixture was then added to water and extracted with 100 milliliters of diethyl ether. The organic phase was dried over anhydrous magnesium sulfate and stripped of solvent, in vacuo, affording a yellow oil which was purified by passage through a column containing 30 grams of silica gel and eluted with hexane followed by diethyl ether. Solvent removal afforded 1.0 gram of colorless, sticky oil confirmed by NMR and MS analyses as the desired product.

Although preparation of certain compounds of the invention have been illustrated by the foregoing Examples, it is to be understood that other compounds of the invention may be readily prepared by those skilled in the art using the same or similar techniques and by varying the choice of starting materials.

Weed control in accordance with this invention is effected by application, either before or after emergence of weeds, of a herbicidally effective amount of a compound of this invention. It is, of course, to be understood that the term "a compound of this invention" also includes mixtures of such compounds.

The term "herbicidally effective amount" is that amount of a compound of this invention required to so injure or damage weeds such that the weeds are incapable of recovering following application. The quantity of a compound of this invention applied in order to exhibit a satisfactory herbicidal effect may vary over a wide range and depends on a variety of factors, such as, for example, hardiness of a particular weed species, extent of weed infestation, climatic conditions, soil conditions, method of application, and the like. Typically, less than one pound per acre of a compound of this invention would be expected to provide satisfactory weed control, although in some instances application rates in excess of one pound per acre; e.g., up to 5 or more pounds per acre might be required. Of course, the efficacy of a particular compound against a particular weed species may readily be determined by routine laboratory or field testing in a manner well known to the art. It is expected that satisfactory weed control can be had at a rate of application in the range of 0.5 to 2.0 pounds per acre.

Of course, a compound of this invention can be formulated according to routine methods with any of several known and commonly used herbicidal diluents, adjuvants and carriers. The formulations can contain liquid carriers and adjuvants such as organic solvents, as well as emulsifiers, stabilizers, dispersants, suspending agents, spreaders, penetrants, wetting agents and the like. Typical carriers utilized in dry formulations include clay, talc, diatomaceous earth, silica and the like. Preferred formulations are those in the form of wettable powders, flowables, dispersible granulates or aqueous emulsifiable concentrates which can be diluted with water at the site of application. Also, dry formulations such as granules, dusts, and the like, may be used.

When desired, a compound of this invention can be applied in combination with other herbicidal agents in an effort to achieve even broader vegetative control. Typical herbicides which can be conveniently combined with Formula I compound include atrazine, hexazinone, metribuzin, ametryn, cyanazine, cyprazine, prometon, prometryn, propazine, simazine, terbutryn, propham, alachlor, acifluorfen, bentazon, metolachlor and N,N-dialkyl thiocarbamates such as EPTC, butylate or vernolate. These, as well as other herbicides described, for example, in the *Herbicide Handbook of the Weed Society of America*, may be used in combination with a compound or compounds of the invention. Typically such formulations will contain from about 5 to about 95 percent by weight of a compound of this invention.

The herbicidal formulations contemplated herein can be applied by any of several methods known to the art. Generally, the formulation will be surface applied as an aqueous spray. Such application can be carried out by conventional ground equipment, or if desired, the sprays can be aerially applied. Soil incorporation of such surface applied herbicides is accomplished by natural leaching, and is, of course, facilitated by natural rainfall and melting snow. If desired, however, the herbicides can be incorporated into the soil by conventional tillage means.

The compounds prepared as described in the Examples were tested for herbicidal efficacy, against a variety of broadleaf weed species, under controlled laboratory conditions of light, humidity and temperature. A solvent solution of said compound was applied postemergence to test flats containing the various weed species, and herbicidal efficacy was determined by periodic visual inspection, after application of the compounds. Herbicidal efficacy was determined on a Numerical Injury Rating scale of from 0 (no injury) to 10 (all plants dead).

A NIR of 7 to 9 indicates severe injury; a NIR of 4 to 6 indicates moderate injury, i.e. plant growth is reduced to the extent that normal growth would be expected only under ideal conditions; and a NIR of 1 to 3 indicates slight injury.

The following table gives the postemergence NIR for the compounds prepared as described in the Examples against each of the broadleaf weed species to which it was applied. The compound was applied at a rate of 1.0 pound per acre and the NIR was determined two weeks after application. The broadleaf (BL) weeds used in the test were coffeeweed (COFE), jimsonweed (JMWD), tall morningglory (MNGY), teaweed (TEAW), velvetleaf (VTLF), sicklepod (SKPD) and lambsquarter (LMBQ).

| BL-Weeds: | Example | | |
|---|---|---|---|
| | I | II | III |
| COFE | 9 | 4 | 6 |
| JMWD | 10 | 10 | 10 |
| MNGY | 10 | 10 | 10 |
| TEAW | 6 | 4 | 5 |
| VTLF | 10 | 5 | 5 |
| SKPD | 2 | 2 | 1 |
| LMBQ | 10 | 10 | 10 |
| Average BL NIR | 8.1 | 6.4 | 6.7 |

Basis these screening tests, compounds of this invention can be effectively used for postemergence control of a wide variety of broadleaf weeds.

Although the invention has been described in considerable detail by the foregoing, it is to be understood that many variations may be made therein by those skilled in the art without departing from the spirit and scope thereof as defined by the appended claims.

What is claimed is:

1. A compound of the formula:

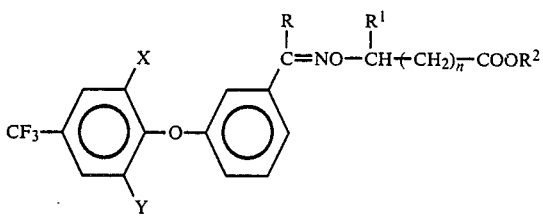

wherein:

X and Y are the same or different halogen;

R is hydrogen, halogen, cyano, $C_1$ to $C_4$ alkyl or haloalkyl, $C_1$ to $C_4$ alkoxy or alkylthio, or mono or dialkylamino;

$R^1$ is hydrogen or $C_1$ to $C_4$ alkyl;

$R^2$ is hydrogen or up to $C_{10}$ alkyl, haloalkyl, cycloalkyl, alkenyl, alkynyl, alkoxyalkyl or phenyl, substituted phenyl, benzyl or substituted benzyl; and n is 0, 1, 2 or 3.

2. A compound of claim 1 wherein X is fluorine or chlorine and Y is fluorine or chlorine.

3. A compound of claim 2 wherein R is alkyl or haloalkyl; $R^1$ is hydrogen; $R^2$ is alkyl or haloalkyl; and n is 0.

4. A herbicidal formulation containing an inert carrier and a herbicidally effective amount of a compound or mixture of compounds defined in claim 1.

5. In a method of controlling weeds wherein a herbicidally effective amount of herbicide is applied to a growth medium prior to emergence of the weeds therefrom or to the weeds subsequent to their emergence from the growth medium, wherein the improvement resides in using as the herbicide a compound or mixture or compounds defined by claim 1.

* * * * *